(12) United States Patent
Alqahtani

(10) Patent No.: US 12,251,477 B1
(45) Date of Patent: *Mar. 18, 2025

(54) SURFACTIN-BASED LIPOPEPTIDE FOR MRNA DELIVERY

(71) Applicant: KING SAUD UNIVERSITY, Riyadh (SA)

(72) Inventor: Mohammed Saeed Alqahtani, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/795,653

(22) Filed: Aug. 6, 2024

Related U.S. Application Data

(62) Division of application No. 18/662,099, filed on May 13, 2024, now Pat. No. 12,186,434.

(51) Int. Cl.
*A61K 9/51* (2006.01)
*C12N 15/88* (2006.01)

(52) U.S. Cl.
CPC .......... *A61K 9/5123* (2013.01); *A61K 9/5169* (2013.01); *A61K 9/5192* (2013.01); *C12N 15/88* (2013.01)

(58) Field of Classification Search
CPC .... C12N 15/58; A61K 9/5153; A61K 9/5169; A61K 9/5192
See application file for complete search history.

(56) References Cited

FOREIGN PATENT DOCUMENTS

| CN | 117084999 A | 11/2023 |
|---|---|---|
| EP | 2572706 A | 3/2013 |
| JP | 2009-221165 A | 10/2009 |
| WO | 202244844 A1 | 11/2022 |
| WO | 2022166747 A1 | 11/2022 |

OTHER PUBLICATIONS

Hou et al, Lipid Nanoparticles for mRNA Delivery, Nat Rev Mater,6(12): 1078-1094. (Year: 2021).*

Y. Huang, et al. "Intracellular delivery of messenger RNA to macrophages with surfactant-derived lipid nanoparticles", DOI: https://doi.org/10.1016/j.mtadv.2022.100295.

* cited by examiner

*Primary Examiner* — Carlos A Azpuru
(74) *Attorney, Agent, or Firm* — Nath, Goldberg & Meyer; Joshua B. Goldberg

(57) ABSTRACT

Surfactin-based lipopeptides for mRNA delivery are made by a method including providing OleSurf lipids to form an organic phase, mixing a mRNA in 100 mM citrate buffer at pH 4 to form an aqueous phase, mixing one part of the organic phase with three parts of the aqueous phase to obtain mRNA loaded lipid nanoparticles, purifying the mRNA loaded lipid nanoparticle platform using dialysis, and purifying the mRNA loaded lipid nanoparticle platform using centrifugal filtration. The OleSurf lipids are made by modifying surfactin with oleylamine. The resulting nanoparticles may be useful as mRNA delivery vehicles.

8 Claims, 10 Drawing Sheets
(1 of 10 Drawing Sheet(s) Filed in Color)

SURFACTIN-BASED LIPOPEPTIDE FOR MRNA DELIVERY

CROSS-REFERENCE TO RELATED APPLICATION

This application is a divisional of U.S. patent application Ser. No. 18/662,099, filed on May 13 2024, the entire contents of which are incorporated herein by reference.

BACKGROUND

Field

The disclosure of the present patent application relates to targeted mRNA delivery and particularly to a surfactin-based lipopeptide for mRNA delivery.

Description of Related Art

Numerous advanced delivery systems have been developed, including protamine, lipid nanoparticles (LNPs), liposomes, polymeric polyplexes, micelles, and dendrimers (Ibba, M. L., et al. 2021. "Advances in mRNA non-viral delivery approaches", *Advanced drug delivery reviews*, 177: 113930.). Among these delivery systems, LNPs have emerged as a highly attractive one for delivering nucleic acid-based drugs (Qin, S., et al. 2022. "mRNA-based therapeutics: powerful and versatile tools to combat diseases", *Signal transduction and targeted therapy*, 7: 166.). Messenger RNA (mRNA) technology holds significant promise for therapeutic applications (Kaczmarek, J. C., et al. 2017. "Advances in the delivery of RNA therapeutics: from concept to clinical reality", *Genome medicine*, 9: 1-16.). An example of an FDA-approved RNA-based therapy is Onpattro (patisiran), a LNP based small-interfering RNA (siRNA) treatment for hATTR amyloidosis (Zhang, X., et al. 2020. "Pharmacokinetics of Patisiran, the first approved RNA interference therapy in patients with hereditary transthyretin-mediated amyloidosis", *The Journal of Clinical Pharmacology*, 60: 573-85.). The main lipid discovered in this LNP is called DLin-MC3-DMA, often referred to as MC3. It consists of a di linoleic acid tail and an ester linker group, making it effective for silencing genes in the liver (Semple, S. C., et al. 2010. 'Rational design of cationic lipids for siRNA delivery', *Nature biotechnology*, 28: 172-76.). Additionally, some RNA-based therapeutics have been developed for coronavirus disease 2019 (COVID-19) vaccines, demonstrating their safety and effectiveness (Food and Drug Administration. 2021. "Fact sheet for healthcare providers administering vaccine (vaccination providers). Emergency use authorization (EUA) of the Janssen COVID-19 vaccine to prevent coronavirus disease 2019 (COVID-19). Silver Spring, MD: US Department of Health and Human Services", *Food and Drug Administration*.). The properties of mRNA, including its instability in an in vivo environment and its inability to permeate cell membranes effectively, hinder its efficient delivery to the cytoplasm, where it carries out its functions (Hajj, K. A, et al. 2020. "A potent branched-tail lipid nanoparticle enables multiplexed mRNA delivery and gene editing in vivo", *Nano letters*, 20: 5167-75.). To enhance mRNA delivery efficiency, extensive research has been dedicated to screening various lipids and refining their properties to further improve efficiency (Zhang, Y., et al. 2021. "Lipids and lipid derivatives for RNA delivery", *Chemical reviews*, 121: 12181-277.). The general structure of lipids can be divided into two main components the headgroup and the tails. Lipid headgroups usually carry a positive charge, primarily composed of amine moieties. This positive charge exhibits pH-dependent ionization, which facilitates the endosomal escape. The size and charge density of the headgroup play crucial roles in capturing the nucleic acid, providing stability to the lipid nanoparticle (LNP), and interacting with the cell membrane.

Moreover, to reduce accumulation and long-term toxicity, lipids should be readily degraded into non-toxic metabolites after successful intracellular delivery, which is especially crucial for mRNA therapeutics requiring repeated dosing (Maier, M. A., et al. 2013. "Biodegradable lipids enabling rapidly eliminated lipid nanoparticles for systemic delivery of RNAi therapeutics", *Molecular Therapy*, 21: 1570-78.).

Over the past 25 years, subsequent studies have extensively explored the capacity of numerous cationic lipids to bind mRNA and facilitate the delivery both in vitro cells and in vivo animal models (Akinc, A., et al. 2008. "A combinatorial library of lipid-like materials for delivery of RNAi therapeutics", *Nature biotechnology*, 26: 561-69.). Initial attempts to use conventional liposomes were hindered by the limited binding between mRNA and neutral or negatively charged liposomes. However, subsequent investigations revealed that the utilization of cationic lipids significantly improved the rates of association and delivery (Tenchov, R., et al. 2021. "Lipid nanoparticles—from liposomes to mRNA vaccine delivery, a landscape of research diversity and advancement", *ACS nano*, 15: 16982-7015.). While the ultimate objective of these investigations is to develop pharmaceutical agents capable of delivering therapeutic mRNA, the initial screening process to identify promising cationic agents typically takes place in cell culture (Zhang et al. 2021). Consequently, in vitro transfection rates serve as a measure of the delivery efficiency of experimental formulations, and the majority of published studies rely solely on cultured cells to evaluate the potential of novel cationic agents for intracellular delivery. Furthermore, aside from the cell type utilized in these studies, it is widely acknowledged that factors such as mixing conditions, charge ratio, particle size, zeta potential, and the presence of serum can have a significant impact on the observed transfection rates in such experiments. Previously, mRNA has been formulated using various cationic delivery platforms. Several studies insisted on the importance of the cationic lipid for mRNA transfection (Maugeri, M., et al. 2019. "Linkage between endosomal escape of LNP-mRNA and loading into EVs for transport to other cells", *Nature communications*, 10: 4333.). The fundamental concept underlying these strategies is to employ cationic lipids (lipidoids) to electrostatically complex the anionic RNA molecules, thereby reducing particle size and aiding cellular uptake. These characteristics make lipid nanoparticles (LNPs) valuable as delivery vehicles for vaccines and other therapeutics especially for large-scale production (Sabnis, S., et al. 2018. "A novel amino lipid series for mRNA delivery: improved endosomal escape and sustained pharmacology and safety in non-human primates", *Molecular Therapy*, 26: 1509-19.).

Biomimetic and bioinspired nanomaterials, such as lipopeptide based nanoparticles, have gained significant attention in the recent years, especially in the drug delivery field (Dong, Y., et al. 2014. 'Lipopeptide nanoparticles for potent and selective siRNA delivery in rodents and nonhuman primates', *Proceedings of the National Academy of Sciences*, 111: 3955-60; Busatto, S., et al. 2020. 'Lipoprotein-based drug delivery', *Advanced drug delivery reviews*, 159: 377-90.). Lipopeptides exhibit characteristics of both lipids and peptides. They possess biological functions, including targeting effects, while also leveraging lipid properties such as hydrophobic interactions (Jing, X., et al. 2016. 'Delivery of siRNA complexed with palmitoylated α-peptide/β-peptoid cell-penetrating peptidomimetics: membrane interaction and structural characterization of a lipid-based nanocarrier system', Molecular pharmaceutics, 13: 1739-49.). Lipopeptides constitute a distinct category of a highly potent biosurfactant. These bioactive secondary metabolites exhibit impressive therapeutic and biotechnological attributes (Gudiña, E. J., et al. 2013. 'Potential therapeutic applications of biosurfactants', Trends in pharmacological sciences, 34: 667-75.). Among these, surfactin, a prominent member of the antimicrobial lipopeptide family, is produced by a *Bacillus subtilis* strain (Lee, J. H., et al. 2012. 'The production of surfactin during the fermentation of cheonggukjang by potential probiotic *Bacillus subtilis* CSY191 and the resultant growth suppression of MCF-7 human breast cancer cells', Food Chemistry, 131: 1347-54.). Surfactin is a cyclic lipopeptide with amphipathic properties and a molecular weight of 1,036 Da (Gudiña et al. 2013). It is chemically identified by a heptapeptide interlinked with a β-hydroxy fatty acid. Because of its amphipathic nature, surfactin demonstrates a broad spectrum of interactions with target cell phospholipid bilayer and holds promise for various medical applications (Gudiña et al. 2013). Surfactin has the ability to destabilize cell membranes and compromise their structure through a range of theoretical mechanisms. These include its potential to integrate into lipid bilayers, alter membrane permeability through ion channel formation, phospholipids solubilization, and micelle formation (Han, Y., et al. 2018. 'Immune lipoprotein nanostructures inspired relay drug delivery for amplifying antitumor efficiency', Biomaterials, 185: 205-18.). Furthermore, through hydrophobic interactions, surfactin can spontaneously infiltrate lipid membranes, leading to changes in the arrangement of hydrocarbon structures and membrane thickness (Janek, T., et al. 2013. 'Lipopeptide biosurfactant pseudofactin II induced apoptosis of melanoma A 375 cells by specific interaction with the plasma membrane', PloS one, 8: e57991.). In addition to its antifungal and antibacterial effects, surfactin can hinder fibrin clot formation, trigger the creation of ion channels in lipid bilayer membranes, inhibit cyclic adenosine monophosphate activity, prevent platelet aggregation, and display antiviral and antitumor properties (Murugan, C., et al. 2016. 'Combinatorial nanocarrier based drug delivery approach for amalgamation of anti-tumor agents in breast cancer cells: An improved nanomedicine strategy', Scientific reports, 6: 34053; Cao, X., et al. 2010. 'Surfactin induces apoptosis in human breast cancer MCF-7 cells through a ROS/JNK-mediated mitochondrial/caspase pathway', Chemico-biological interactions, 183: 357-62; Sivapathasekaran, C., et al. 2010. 'Marine bacterium derived lipopeptides: characterization and cytotoxic activity against cancer cell lines', International Journal of Peptide Research and Therapeutics, 16: 215-22.). Additionally, surfactin has found application in pharmaceutical formulations to improve the delivery of therapeutic agents. (Kural, F. H., and GUrsoy, R. N. 2011. 'Formulation and Characterization of Surfactin-Containing Self-Microemulsifying Drug Delivery Systems SF-SMEDDS', Hacettepe University Journal of the Faculty of Pharmacy: 171-86; Huang, W., et al. 2018. 'Surfactin-based nanoparticles loaded with doxorubicin to overcome multi-drug resistance in cancers', International journal of nanomedicine: 1723-36.).

Previous studies with mRNA LNPs insisted on the importance of developing a new lipidoid for mRNA transfection. Nonetheless, significant disadvantages associated with frequently used cationic lipids for mRNA delivery include their restricted electrostatic interaction with mRNA due to the presence of a single quaternary ammonium head group (in contrast to structures containing multiple amine functionalities), the activation of the innate immune system leading to undesirable side effects, and unfavorable biodistribution resulting from plasma protein binding and non-specific tissue distribution (Lv, H., et al. 2006. 'Toxicity of cationic lipids and cationic polymers in gene delivery', Journal of controlled release, 114: 100-09.). These factors ultimately contribute to a relatively limited therapeutic window.

Thus, a surfactin-based lipopeptide for mRNA delivery solving the aforementioned problems is desired.

SUMMARY

The purpose of the present study was to synthesize a novel modified surfactin (OleSurf), which serves as a primary component for lipid nanoparticles (LNPs). In our effort to establish correlations for LNP performance, we conducted a comparative analysis of OleSurf LNPs. We assessed their effectiveness in transfecting cell lines in vitro, observed their cellular uptake, and evaluated in vivo expression.

In an embodiment, the surfactin-based lipopeptide for mRNA delivery may be made by a method including providing OleSurf lipids to form an organic phase, mixing a mRNA in 100 mM citrate buffer at pH 4 to form an aqueous phase, mixing one part of the organic phase with three parts of the aqueous phase to obtain mRNA loaded lipid nanoparticles, purifying the mRNA loaded lipid nanoparticle platform using dialysis, and purifying the mRNA loaded lipid nanoparticle platform using centrifugal filtration.

In a further embodiment, the OleSurf lipids may be made by a method including mixing surfactin dissolved in methanol with 2 mmol oleylamine to obtain a reaction mixture, adjusting the pH of the reaction mixture to 8.0 with NaOH, adding 10 ml dichloromethane to the reaction mixture under a nitrogen atmosphere, stirring the reaction mixture at about 25° C. for about 24 hours, concentrating the reaction mixture by evaporation; and purifying the reaction mixture using silica column chromatography to obtain the OleSurf lipids.

In a further embodiment, the surfactin-based lipopeptide for mRNA delivery is formulated as OleSurf nanoparticles encapsulating mRNA for deliver of the mRNA. In this embodiment, the surfactin-based lipopeptide for mRNA delivery may have an average particle size of 84.91±6.24 nm, a polydispersity index of 0.102±0.025, a zeta potential of +1.3±0.7, and an encapsulation efficiency of 90.51%±3.7%.

In a further embodiment, the surfactin-based lipopeptide for mRNA may be used in a method of delivering mRNA to a subject in need thereof, comprising administering the lipid nanoparticle platform to the subject in need thereof. In this embodiment, the mRNA may be any mRNA that the subject is in need of, including but not limited to a mRNA having a specific therapeutic activity (such as a mRNA that may be transcribed upon entry into the cell to produce a desired protein, mRNA that may modify the processing of other mRNA, such as anti-sense mRNA, or mRNA that may act as a vaccine or immune-stimulatory agent, or any other mRNA for which delivery into a subject is desired).

These and other features of the present subject matter will become readily apparent upon further review of the following specification.

BRIEF DESCRIPTION OF DRAWINGS

The patent or application file contains at least one drawing executed in color. Copies of this patent or patent application publication with color drawing(s) will be provided by the Office upon request and payment of the necessary fee.

Similar reference characters denote corresponding features consistently throughout the attached drawings.

DETAILED DESCRIPTION

Figure 1A:
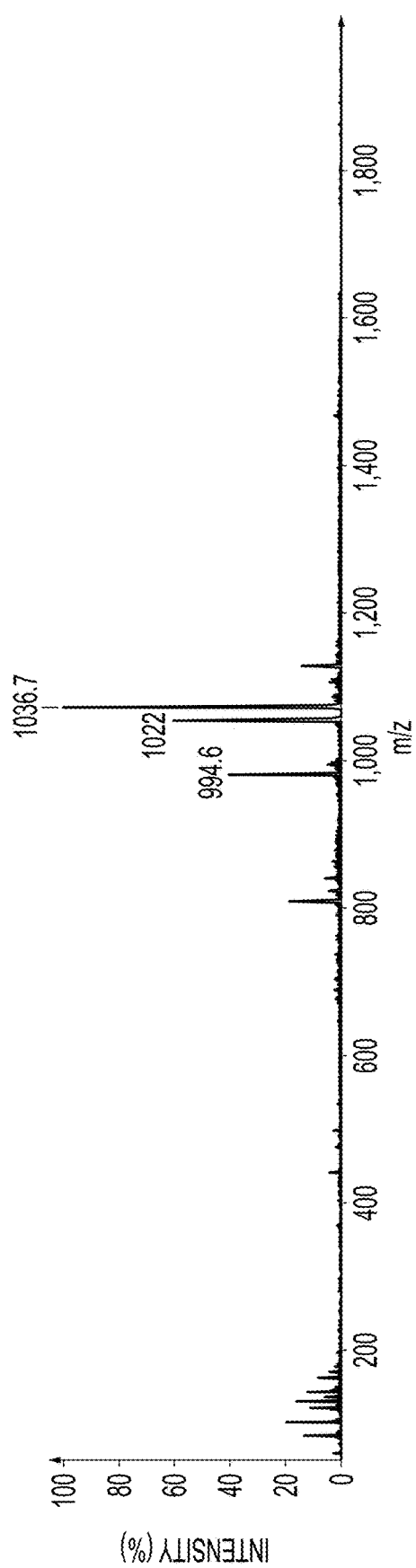
FIGS. 1A and 1B depict high-resolution mass spectrometry (HRMS) ESI of (1A) Surfactin ($C_{53}H_{93}N_7O_{13}$) showing the main m/z (M+H) at 994.6, 1008.5, 1022 and 1036.7 (1B) OleSurf ($C_{89}H_{163}N_9O_{11}$) calc. 1535 found 1535.2.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

As used herein, the terms "OleSurf" and "OleSurf lipids" refer to surfactin modified by oleylamine according to one of the specific methods disclosed herein.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Throughout this application the term "mRNA" is used for the RNA that is delivered by the lipid nanoparticle platform. However, one of ordinary skill in the art would understand that the lipid nanoparticle platform disclosed herein would be effective to deliver any kind of ribonucleic acid. Accordingly, the term mRNA" as used herein is not limited to the traditional messenger RNA, but encompasses any form of ribonucleic acid having a roughly equivalent size and charge to a traditional mRNA molecule.

The purpose of the present study was to synthesize a novel modified surfactin (OleSurf), which serves as a primary component for lipid nanoparticles (LNPs). In our effort to establish correlations for LNP performance, we conducted a comparative analysis of OleSurf LNPs. We assessed their effectiveness in transfecting cell lines in vitro, observed their cellular uptake, and evaluated in vivo expression.

In an embodiment, the surfactin-based lipopeptide for mRNA delivery may be made by a method including providing OleSurf lipids to form an organic phase, mixing a mRNA in 100 mM citrate buffer at pH 4 to form an aqueous phase, mixing one part of the organic phase with three parts of the aqueous phase to obtain mRNA loaded lipid nanoparticles, purifying the mRNA loaded lipid nanoparticle platform using dialysis, and purifying the mRNA loaded lipid nanoparticle platform using centrifugal filtration.

In an embodiment, the dialysis step for purifying the mRNA loaded lipid nanoparticle platform may be achieved using previously hydrated dialysis cassettes in 1× phosphate buffered saline solution for at least twelve hours.

In an embodiment, the centrifugation step for purifying the mRNA loaded lipid nanoparticle platform may be achieved using centrifugal filtration and 10 kDa centrifuge filters at 3000 g for 60 minutes.

In a further embodiment, the OleSurf lipids may be made by a method including mixing surfactin dissolved in methanol with 2 mmol oleylamine to obtain a reaction mixture, adjusting the pH of the reaction mixture to 8.0 with NaOH, adding 10 ml dichloromethane to the reaction mixture under a nitrogen atmosphere, stirring the reaction mixture at about 25° C. for about 24 hours, concentrating the reaction mixture by evaporation; and purifying the reaction mixture using silica column chromatography to obtain the OleSurf lipids.

In a further embodiment, the surfactin-based lipopeptide for mRNA delivery is formulated as OleSurf nanoparticles encapsulating mRNA for delivery of the mRNA. In this embodiment, the surfactin-based lipopeptide for mRNA delivery may have an average particle size of 84.91±6.24 nm, a polydispersity index of 0.102±0.025, a zeta potential of +1.3±0.7, and an encapsulation efficiency of 90.51%±3.7%.

In a further embodiment, the surfactin-based lipopeptide for mRNA may be used in a method of delivering mRNA to a subject in need thereof, comprising administering the lipid nanoparticle platform to the subject in need thereof. In this embodiment, the mRNA may be any mRNA that the subject is in need of, including but not limited to a mRNA having a specific therapeutic activity (such as a mRNA that may be transcribed upon entry into the cell to produce a desired protein, mRNA that may modify the processing of other mRNA, such as anti-sense mRNA, or mRNA that may act as a vaccine or immune-stimulatory agent, or any other mRNA for which delivery into a subject is desired).

The surfactin-based lipopeptide for mRNA delivery may be better understood in view of the following examples.

Materials

Surfactin was obtained from (TargetMol, Boston, MA, USA). Lipofectamine 2000 (LP 2000) was from (Invitrogen, CA, USA). 1,2-distearoyl-snglycero-3-phosphocholine (DSPC) was acquired from Avanti Polar Lipids (Birmingham, AL, USA). Cholesterol was purchased from MP Biomedicals (Santa Ana, CA, USA). 1,2-dimyristoyl-rac-glycero-3-methoxypolyethylene glycol-2000 (DMG-PEG) was from NOF America Corporation (White Plains, NY, USA). Pierce D-Luciferin, Slide-A-Lyzer™ MINI Dialysis Device (MWCO, 10 KDa), RNAse-free, and Quanti-iT Ribogreen RNA reagent were purchased from Thermo Fisher Scientific (Waltham, MA, USA). Firefly luciferase (Fluc) mRNA was purchased from Trilink Biotechnologies (San Diego, CA, USA). The firefly-luciferase mRNA labeled with the fluorophore Cy5 was purchased from APExBIO. Microfluidic cartridges for the NanoAssmblr™ were purchased from Precision Nanosystems. The ONE-Glo Luciferase Assay kit was purchased from Promega Corporation. Dulbecco's Modified Eagle Medium (DMEM), Fetal Bovine Serum (FBS), Dlin-MC3-DMA (MC3), sodium hydroxide, citric acid, sodium citrate and oleylamine were obtained from Sigma-Aldrich (St. Louis MO, USA). Hoechst 33342 was purchased from Life Technologies (Carlsbad, CA, USA). LysoBrite green was obtained from AAT Bioquest (Sunnyvale, CA, USA). All other chemicals were of reagent grade.

Synthesis and Characterization of Lipopeptide Conjugates

Oleylamine was used to modify surfactin via amidation reactions as previously reported (Morikawa, M., et al. 2000. 'A study on the structure-function relationship of lipopeptide biosurfactants', *Biochimica et Biophysica Acta (BBA)-Molecular and Cell Biology of Lipids*, 1488: 211-18.) and its structure was confirmed by NMR and mass spectrometer. 1H NMR spectra were measured on a 300 & 500 MHz Varian spectrometer using TMS as internal standard. Mass spectra were measured on an AVANT UHPLC system equipped with an Advion expression® S compact mass spectrometer (Advion, Ithaca, NY, USA). Briefly, twenty milligrams of surfactin was dissolved in methanol and mixed with (0.25 g, 2 mmol) of Oleylamine. After adjusting the pH to 8.0 with 2 M NaOH, 10 ml of dichloromethane (DCM) was added to start the reaction under nitrogen atmosphere. The reaction mixture was stirred at 25° C. for 24 h. Finally, the reaction mixture was concentrated by evaporator and purified with silica column chromatography (DCM/MeOH 10:1 v/v). Yellow oil was obtained and was sealed and stored at 4° C. until further use.

Lipid Nanoparticle (LNP) Formulation and Characterization

LNPs were formulated via microfluidic mixing using a previously described method with some modifications (Kim, J., et al. 2020. 'Naturally derived membrane lipids impact nanoparticle-based messenger RNA delivery', *Cellular and molecular bioengineering*, 13: 463-74.). Briefly, one-part of organic phase was mixed with three parts aqueous phase (containing the mRNA). The organic phase consisted of the cationic lipid, DSPC, DMG-PEG2k, and cholesterol at a molar ratio of 50:15:30:2 respectively. The aqueous phase consisted of the mRNA in 100 mM Citrate buffer pH 4. Then, the mRNA-LNPs were purified using previously hydrated dialysis cassettes. The cassettes containing the mRNA-LNPs were left in a 1.0-liter beaker containing 1×PBS and dialyzed for a minimum of 12 h. After dialysis, the dialysis cassettes containing the mRNA-LNPs were kept into a sterile biosafety cabinet, and the mRNA-LNPs was removed using a syringe with a needle. Finally, the formulation was further purified using Amicon Ultra centrifugal filters (10 kDa, 3000 g, 60 min) and stored at 4° C. The hydrodynamic radius (nm) and polydispersity index (PDI) of the LNPs were assessed through dynamic light scattering using the Malvern Zetasizer-S 3600 (Malvern Instruments Inc., Southborough, MA, USA). Each sample was measured in triplicate, and the results are expressed as mean±SD. The efficiency of mRNA encapsulation was determined using a modified version of the Quant-iT RiboGreen RNA reagent (as described in detail by Aranda IV, et al. 2009. 'Comparison and evaluation of RNA quantification methods using viral, prokaryotic, and eukaryotic RNA over a 104 concentration range', *Analytical biochemistry*, 387: 122-27.). Encapsulation efficiency was expressed as % mean of three experiments (±SD).

Cryo-TEM Image Analysis

Cryo-TEM acquisition was performed at 300 kV using FEI Titan Krios (Thermo Fisher Scientific) equipped with Falcon III and K3 cameras with DED. 3-5 µl of the sample was dispensed on a plasma cleaned grid (Quantifoil TEM grids) in the Vitrobot chamber and allowed to incubate for 50 s. The chamber was set to 100% humidity at 4° C. Next, the sample was blotted for 4.5 s and then plunged into propane-ethane mixture (40% ethane and 60% propane) cooled by liquid nitrogen. Subsequently, the frozen grids observed for any defects and were stored in liquid nitrogen. Transmission electron microscopy (JEM-F200 TEM, USA) was used to detect the morphology of mRNA-encapsulating LNPs. The images obtained were subjected to analysis using ImageJ software.

Cell Culture

HeLa and HepG2 cell lines were obtained from rom the American Type Culture Collection (ATCC) (Rockville, MD, USA). The cells were cultured in Dulbeccos modified Eagles medium (DMEM) containing 10% FBS, 100 mg/mL streptomycin and 100 units/mL penicillin. Cells were grown in a humidified atmosphere and controlled temperature at 37° C. with 5% $CO_2$. Cells at exponential growth were harvested using 0.25% Trypsin-EDTA treatment. In every experiment conducted, consideration is given to the passage number of cells, and after passage 10, the cells are no longer used.

In Vitro Transfection and Uptake Assay

The transfection was performed as previously reported. 6,000 HeLa cells were seeded in each well of a white-wall clear bottom 96-well plate in 100 L of complete cell culture medium (DMEM supplemented with 10% fetal bovine serum and 1% penicillin-streptomycin). The cells were left to adhere overnight in a controlled CO2 incubator at 37° C. and 5% CO2 to ensure ~80% confluent cultures. Transfection using Lipofectamine 2000 was performed according to the manufacturer. The LNP formulations encapsulating firefly luciferase-encoding were diluted in complete cell culture medium so that the total dose is delivered in 100 µL. Briefly, on the day of experiment, the medium was removed from the wells. Next, the cells were treated with either mRNA-LNPs diluted in complete cell culture medium at the desired doses or complete medium (control). After that the 96-well plate containing the treated cells was placed back into the controlled CO2 incubator for 24 hours. The transfection efficiency was calculated by performing a luciferase assay. The 1× cell lysis buffer and luciferase reagent were prepared as per the manufacturer's instructions. The 96-well plate containing the cells was removed from the incubator and placed in a biosafety cabinet. Finally, L of the previously prepared luciferase assay reagent was added. The plate was placed into a Tecan plate reader to measure the bioluminescent signal of each well. Normalized luciferase expression was quantified by subtracting bioluminescence values from untreated cells untreated or transfected cells without firefly luciferase-encoding mRNA cargo.

At the end of incubation, cells were scrapped from the wells and washed three times with cold buffer. Samples were analyzed using flow cytometry (FACS, BD biosciences, CA, USA), and mean fluorescence intensity of the cells was recorded at 10,000 events.

Endosomal Escape Imaging

For endosomal escape studies, the cells were seeded in confocal dishes at a density of $1\times10^5$ cells. Then cells were transfected with LNP formulations and incubated for 0.5, 2 and 4 hours. Next, the treated cells were fixed with 4% paraformaldehyde and washed with phosphate-buffered saline (PBS). Then, they were given three washes with buffer (10×PBS) and were incubated for 45 min with Hoechst and LysoBrite Green. Subsequently, cells were incubated then washed with PBS and kept in buffer (PBS) until imaging. The fluorescence signals of these cells were analyzed by CLSM.

In Vivo Bioluminescence Imaging of LNP

All procedures performed in animals were approved by the Animal Care and use committee of King Saud University (Ethics Ref No. KSU-SE-20-10) and performed according to the National Institutes of Health Guidelines for the Care and Use of Laboratory Animals. Female BALB/c mice approximately 6-8 weeks of age were obtained from Charles River Laboratories (Wilmington, MA, USA). mRNA-LNP solution was diluted with sterile 1×PBS prior to in vivo administration. Randomized mice received tail injections of 100 µl of luciferase LNPs at a dose of 0.15 mg $kg^{-1}$. For in vivo imaging, a stock solution of 15 mg/mL d-luciferin potassium salt in sterile 1×PBS was prepared. 8, 24, 48 hours post injection, mice were injected with a 200 µL of d-luciferin intraperitoneally. Mice were anesthetized in a chamber with an oxygen flowrate of 2.0 L/min and 2.5% isoflurane prior to imaging. A period of 15 min was allowed for the luciferase signal to stabilize before imaging the treated mice. Then, mice were imaged in an IVIS spectrum optical imager (Perkin Elmer, MA, USA) at 30 sec exposure time to obtain a full bioluminescence image. Moreover, bioluminescence of organs (kidneys, liver, spleen, heart, and lungs) was obtained at 24 hours and was quantified as average radiance (p s-1 cm-2 sr-1). For liver toxicity studies, blood samples were collected 24 hours post injection and sent for biochemistry analysis using Cobas 6000 (Roche Diagnostics, IN, USA). Complete blood count was performed using Sysmex XE 2100 (Sysmex, Kobe, Japan). Spleen and liver samples were taken for histological diagnosis (as described in detail by Baraaj, A. H. 2021. 'Histological, biochemical and DNA changes in the liver of male albino rats treated with silver nanoparticles', *Nano Biomedicine and Engineering*, 13: 20-26.).

Data Analysis

All the experiments were performed in triplicate, and the results are expressed as mean±SD. One-way ANOVA (GraphPad software, CA, USA) was used to compare the effect between different groups, and the results were considered to be significant at $p<0.05$.

Figure 1B:
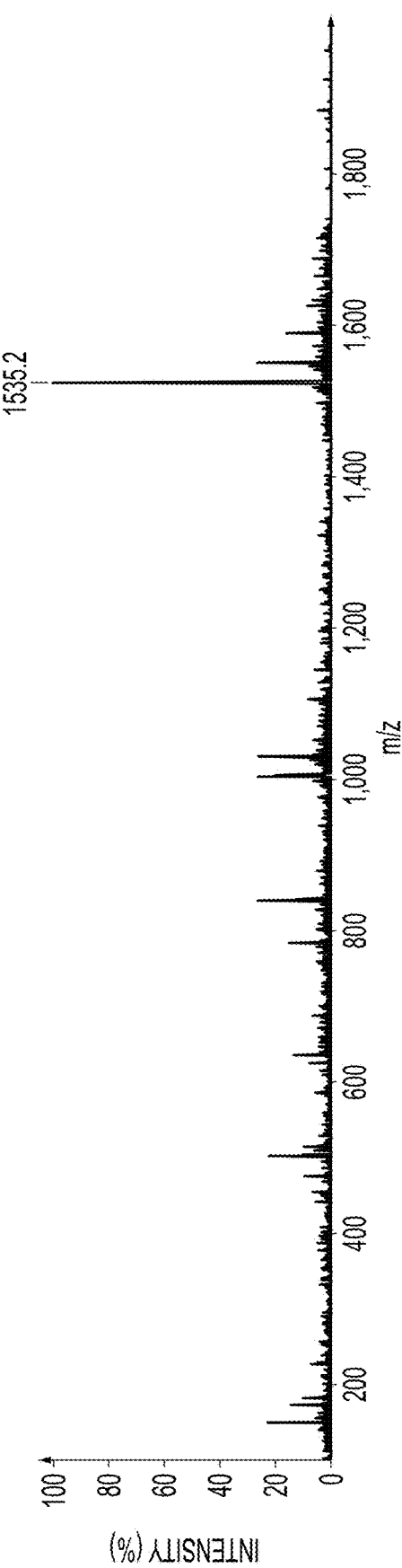
Figure 4:
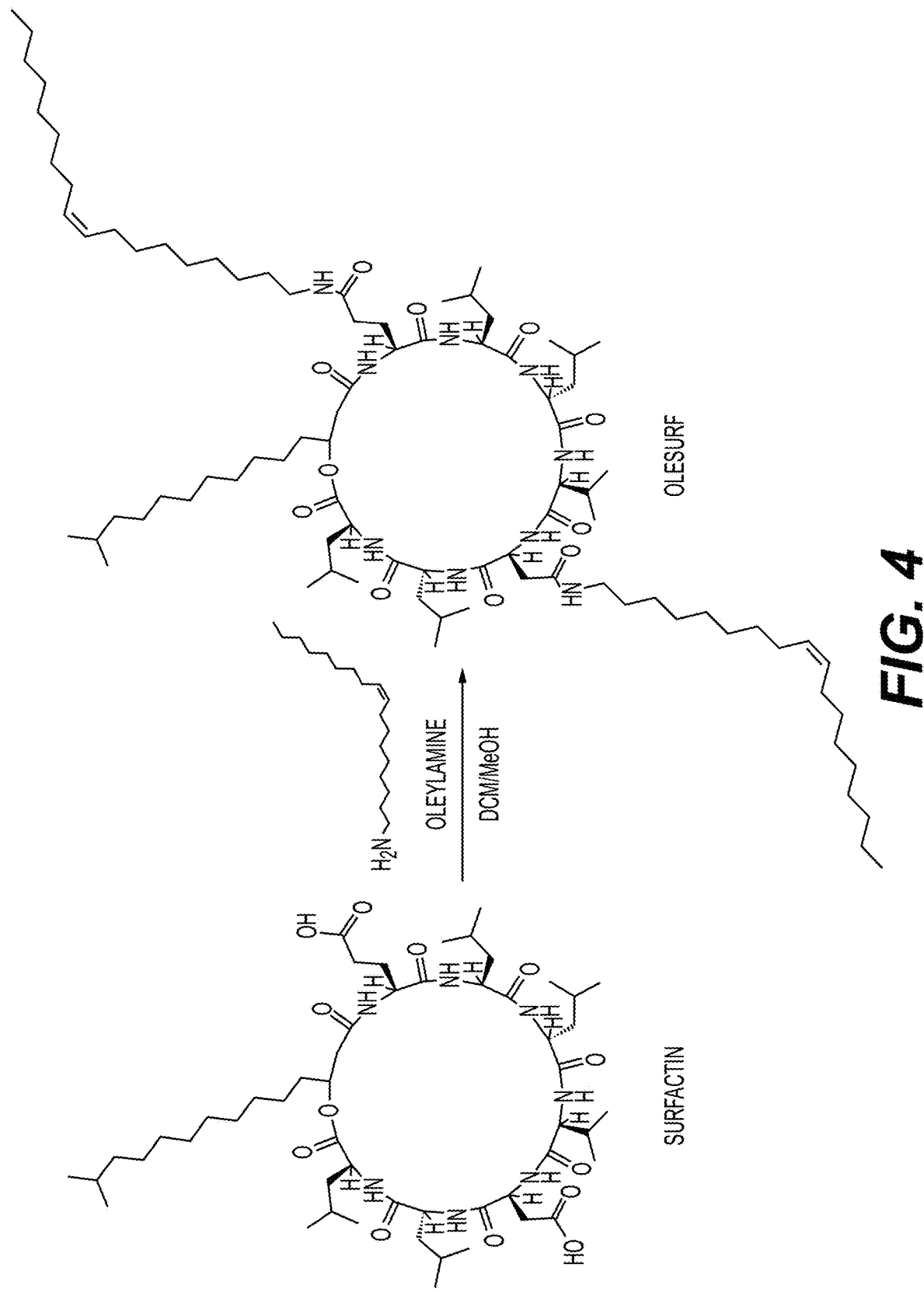
FIG. 4 depicts the synthetic route for synthesis of modified surfactin (OleSurf) via an amidation reaction.

Surfactin is a cyclic lipopeptide (see FIG. 4) of seven hydrophobic amino acids and 3-hydroxy fatty acids. The overall charge of surfactin is slightly negative due to the presence of carboxyl groups of aspartic acid and glutamic acid. OleSurf was synthesized first as a main ingredient of the LNPs with the net yields of (1.8 g, 72%). An amidation method was used to conjugate Oleylamine to the amino acids of surfactin (FIG. 4). Mass spectrometric analysis confirmed the successful synthesis of OleSurf with a molecular weight comparable to the theoretically calculated one (FIGS. 1A-1B). Several studies indicate that esterification or amidation of the two main carboxylic acids of surfactin can result in new derivatives with unique biological and interfacial activities (Morikawa et al. 2000; Bonmatin, J., et al. 2003. 'Diversity among microbial cyclic lipopeptides: iturins and surfactins. Activity-structure relationships to design new bioactive agents', Combinatorial chemistry & high throughput screening, 6: 541-56.). In our study we hypothesized that amidation of aspartic and glutamic acid eliminate the negative charge of those residues and subsequently increases the cationic backbone for mRNA complexation. The major drawbacks of commonly used lipidoids is limited electrostatic interaction with mRNA due to the presence of a single quaternary ammonium head group (Lv et al. 2006). However, surfactin structure contain multiple amine functionalities have been previously reported to bind to RNA (Krishnamurthy, M., et al. 2007. 'Macrocyclic helix-threading peptides for targeting RNA', Angewandte Chemie International Edition, 46: 7044-47.; Pai, J., et al. 2016. 'Screening of pre-miRNA-155 binding peptides for apoptosis inducing activity using peptide microarrays', Journal of the American Chemical Society, 138: 857-67.; Lunde, B. M., et al. 2007. 'RNA-binding proteins: modular design for efficient function', Nature reviews Molecular cell biology, 8: 479-90.). Furthermore, incorporating oleylamine lipid chains, in addition to the predominantly hydrophobic amino residues, will facilitate the complexation process. There are reports indicating that including unsaturated fatty acids as lipid tails has led to increased delivery efficiency in LNP formulations. This is potentially due to their lower transition temperature and their ability to enhance membrane fluidity (Mahato, R. I. 2005. 'Water insoluble and soluble lipids for gene delivery', Advanced drug delivery reviews, 57: 699-712.). Indeed, the overall zeta potential of OleSurf LNPs was increased and mRNA encapsulation efficiency was 90.5% with mRNA concentration of (43.25 g/μL), which is comparable to the common lipid D-Lin-MC3-DMA (MC3). OleSurf when formulated in LNPs resulted in particles of 85 nm and low polydispersity with a positive zeta potential (Table 1).

TABLE 1

Physicochemical characterization of LNPs.

| Sample ID | Average particle size (nm) | Polydispersity index (PDI) | Zeta potential (mV) | Encapsulation efficiency (%) |
|---|---|---|---|---|
| LP2000 | 227.12 ± 11.05 | 0.218 ± 0.103 | −2.05 ± 1.4 | 88.38 ± 4.8 |
| MC3 | 71.61 ± 5.52 | 0.074 ± 0.029 | +5.14 ± 1.6 | 92.35 ± 2.1 |
| OleSurf | 84.91 ± 6.24 | 0.102 ± 0.025 | +1.3 ± 0.7 | 90.51 ± 3.7 |

Figure 5B:
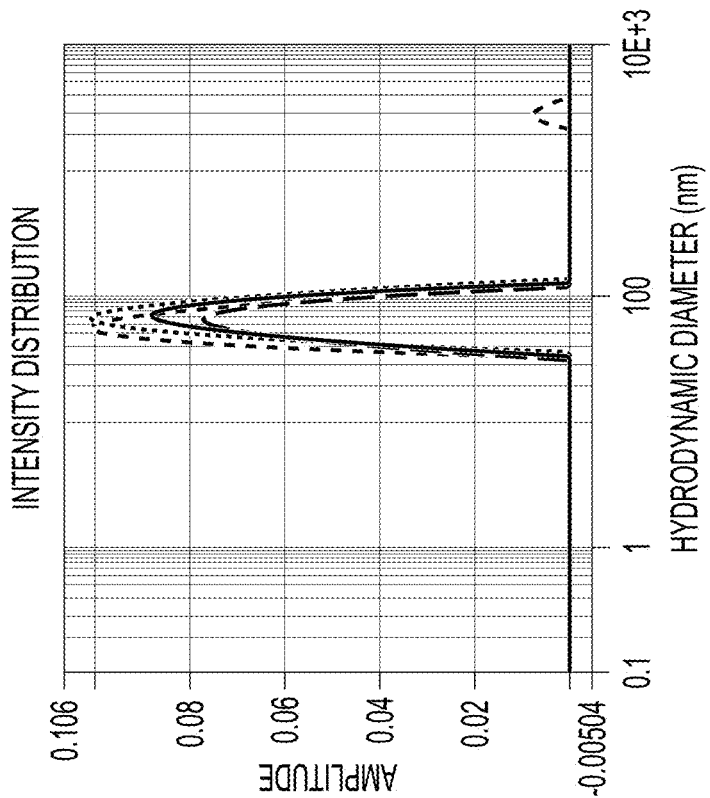
FIGS. 5A-5C depict physicochemical characterization of mRNA OleSurf LNPs, including two graphs (5A & 5B) depicting hydrodynamic size measurements and size distribution by dynamic light scattering (DLS), and (5C) a representative cryoTEM image.
Figure 5A:
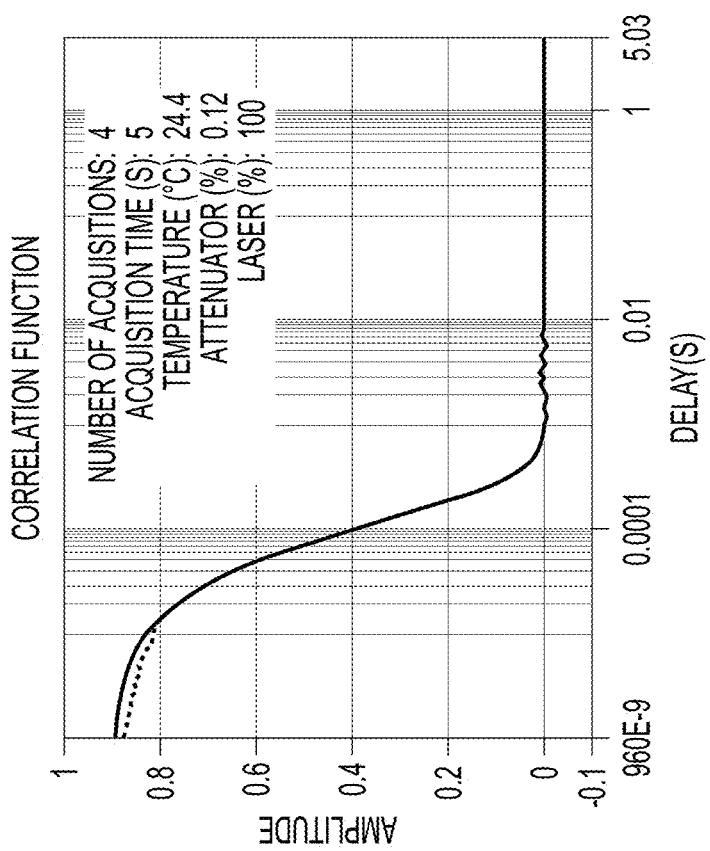
Figure 5C:
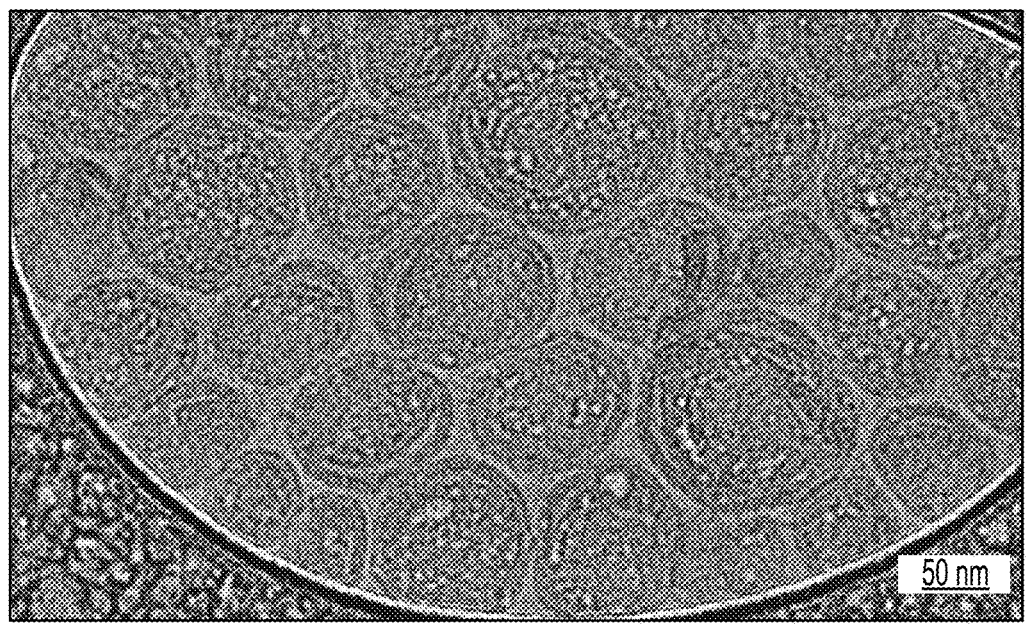

The dynamic light scattering results, along with Cryo-TEM images, indicate colloidal stability (FIGS. 5A-5C). The physicochemical characteristics of LNPs, such as particle diameter, polydispersity index (PDI), and surface charge (zeta potential), play a significant role in determining their biological effectiveness (Breznan, D., et al. 2018. 'Physicochemical properties can be key determinants of mesoporous silica nanoparticle potency in vitro', ACS nano, 12: 12062-79.). Existing research has highlighted the substantial impact of these physicochemical characteristics on the overall success of LNPs in gene delivery (Chen, S., et al. 2016. 'Influence of particle size on the in vivo potency of lipid nanoparticle formulations of siRNA', Journal of controlled release, 235: 236-44.). As LNPs can undergo changes in their particle properties over time during storage, potentially affecting their biological performance, we conducted measurements to track alterations in particle size and zeta potential over a seven-day period while keeping the samples refrigerated. Remarkably, no noticeable differences in terms of size, PDI, or charge were observed during this storage period (data not shown).

Figure 6A:
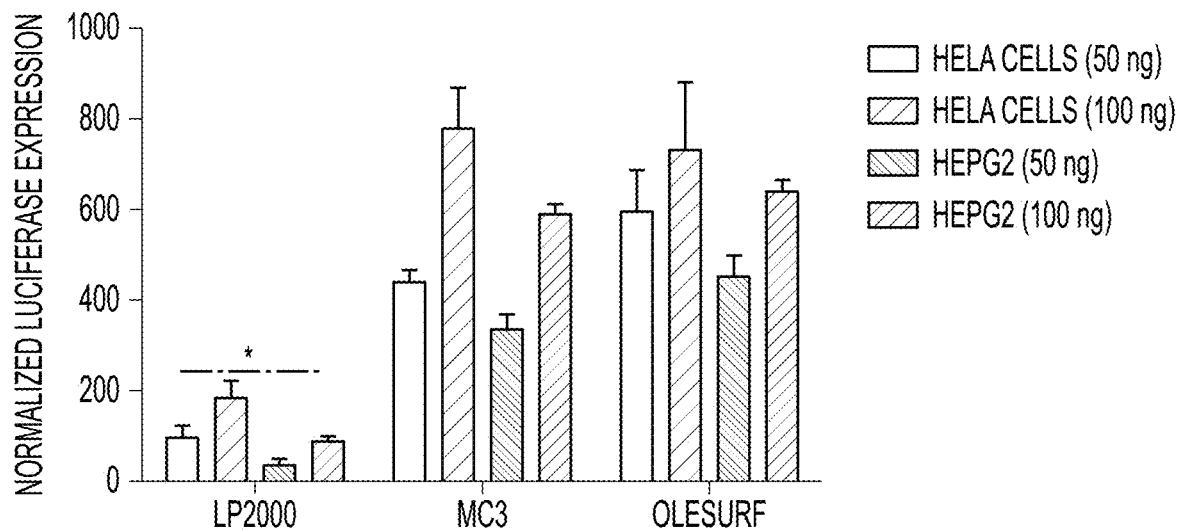
FIGS. 6A and 6B depict graphs illustrating in vitro LNP-mediated luciferase mRNA transfection, including (6A) normalized luciferase expression reported as mean±SD (n=4), and (6B) cell viability for each treatment condition is reported as mean±SD (n=4).
Figure 6B:
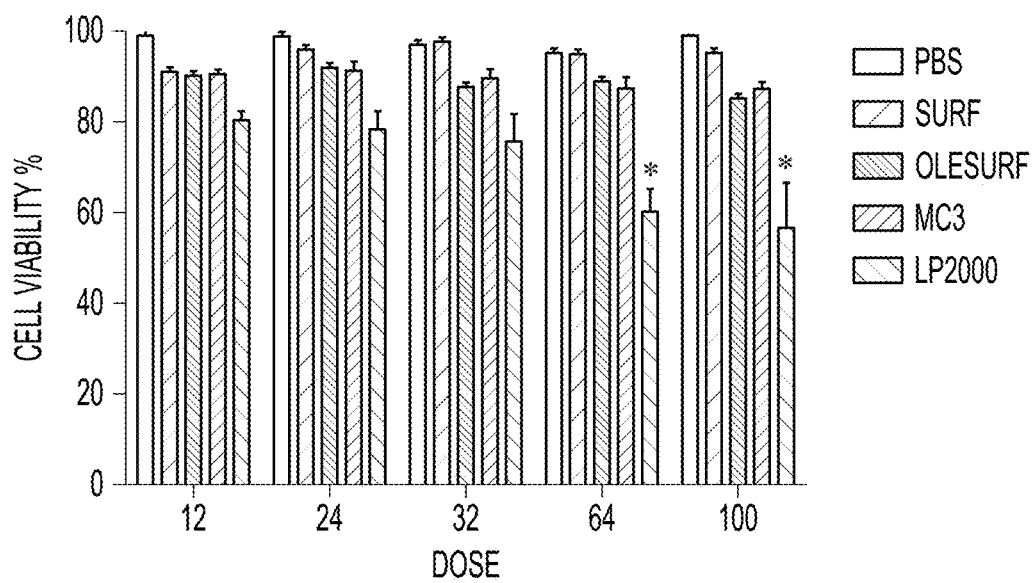
Figure 7A:
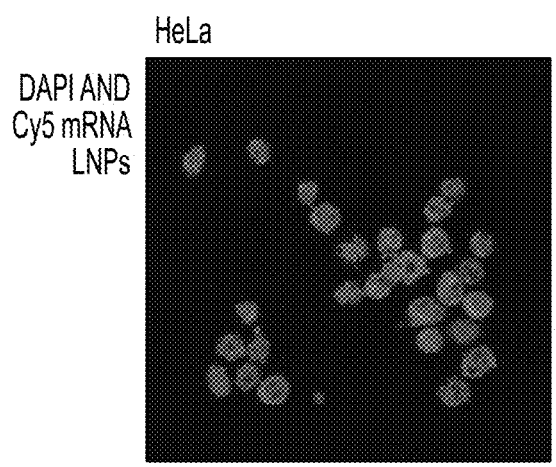
FIGS. 7A-7F depict OleSurf LNP mediated endosomal escape and cytosolic release of Cy5 mRNA in HeLa and HepG2 cell lines. These fluorescent images depict DAPI and Cy5 mRNA LNP staining in HeLa (7A) and HepG2 (7B) cells; endosome staining in Hela (7C) and HepG2 (7D) cells; and merged images of FIGS. 7A and 7C (7E), and of FIGS. 7B and 7D (7F).
Figure 7B:
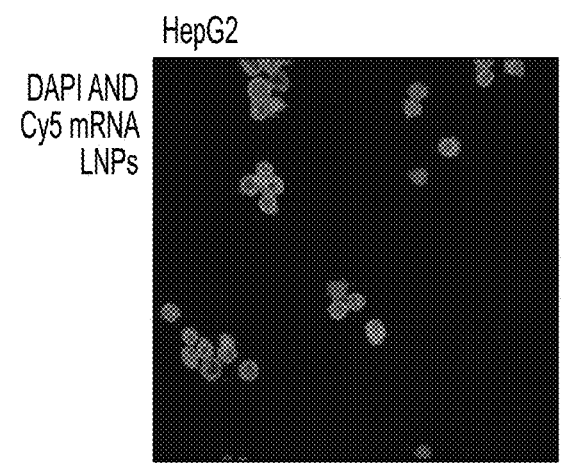
Figure 7C:
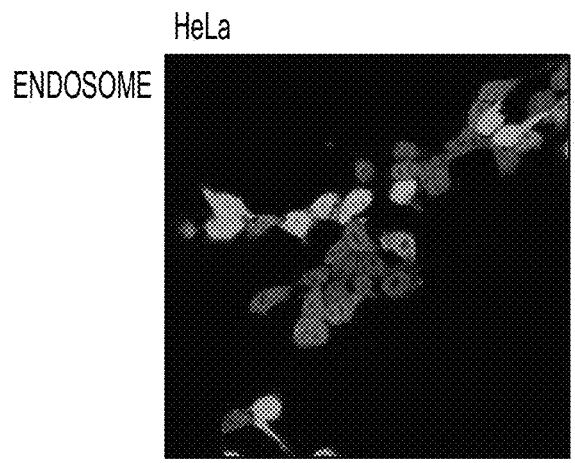
Figure 7D:
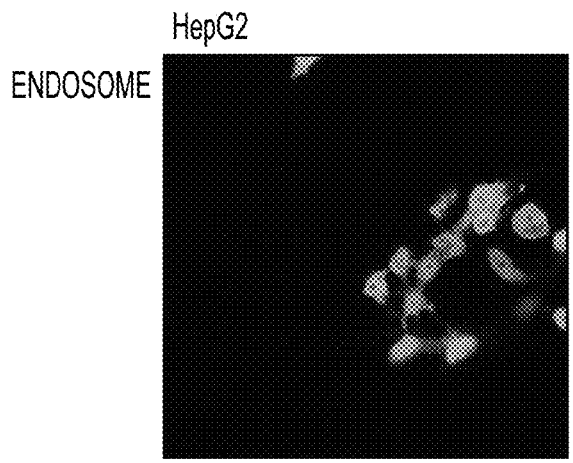
Figure 7E:
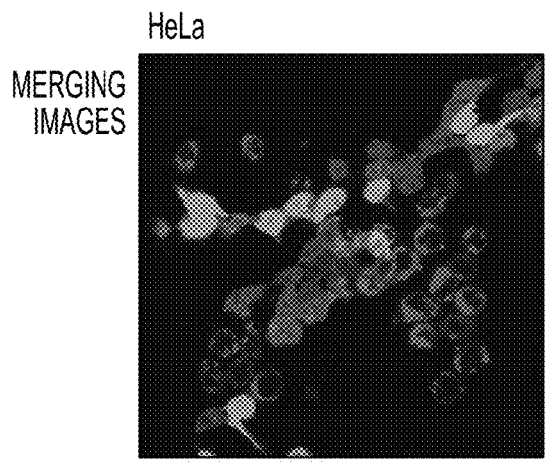
Figure 7F:
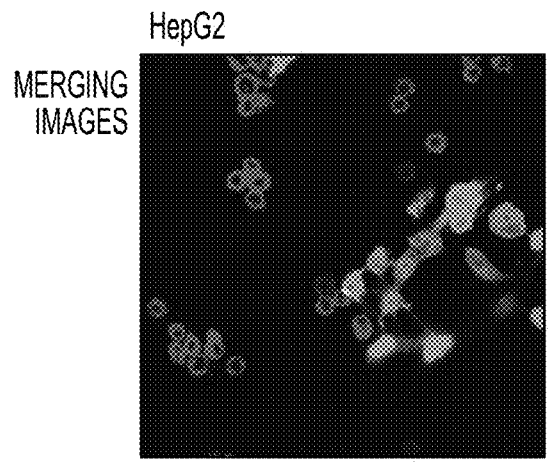
Figure 8:
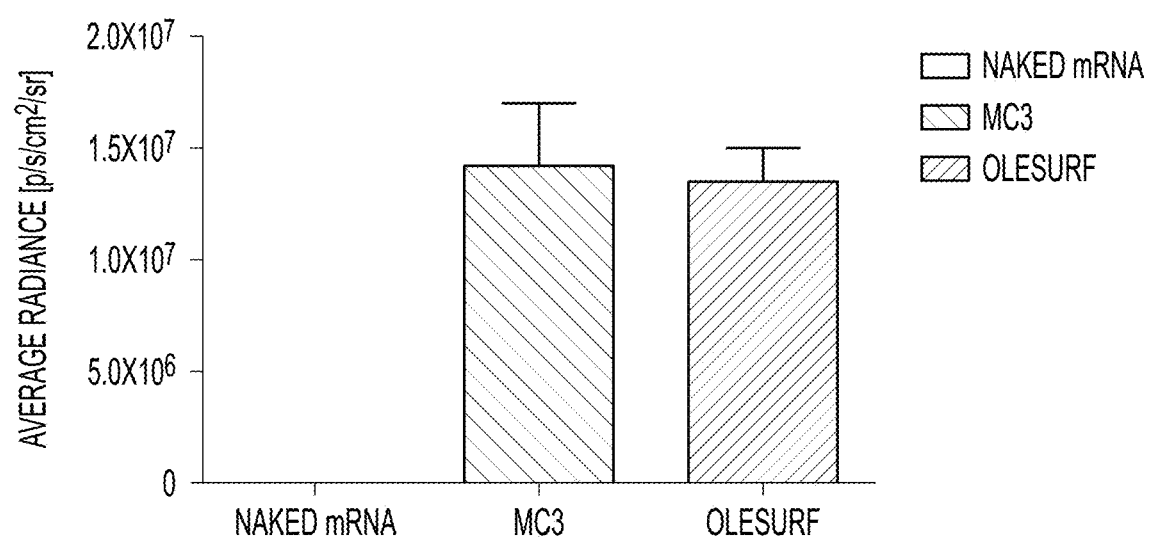
FIG. 8 depicts a graph comparing the average radiance detected in a luciferase assay when transfecting cells with naked mRNA, MC3, and OleSurf.

The cellular transfection efficiency study was carried out using two different cells lines, HeLa and HepG2 cells which are often used for in vitro transfection studies. Luciferase expression as a measure of functional mRNA transfection was evaluated in vitro. Lipofectamine is commonly regarded as the benchmark transfection agent for delivering nucleic acids in vitro (Cardarelli, F., et al. 2016. 'The intracellular trafficking mechanism of Lipofectamine-based transfection reagents and its implication for gene delivery', Scientific reports, 6: 25879.). Furthermore, as a gold standard, our OleSurf LNPs were evaluated against LNPs containing the FDA-approved lipid D-Lin-MC3-DMA (MC3 LNPs) while encapsulating the same Fluc mRNA components (Ni, R., et al. 2019. 'Synthetic approaches for nucleic acid delivery: choosing the right carriers', Life, 9: 59.; Garber, K. 2018. 'Alnylam launches era of RNAi drugs', Nature biotechnology, 36: 777-79.). LNPs or Lipofectamine 2000 (LP2000) were used to treat the cells with two doses of 50 ng or 100 ng of luciferase mRNA per 6000 cells. OleSurf LNPs exhibited significantly higher luciferase expression compared to Lipofectamine, with approximately a threefold increase in transfection efficiency (FIG. 6A). Moreover, the trends observed in the transfection at 50 ng of mRNA were also observed at higher doses of 100 ng, indicating better transfection and a lack of cytotoxicity. Additionally, cell viability was evaluated 24 hours after treatment with different concentrations, and none of the OleSurf LNPs showed a significant decrease in cell viability when compared to MC3 LNPs. However, we noticed that LP2000 induced cytotoxicity in HepG2 cells leading to only 65-70% viable cells after transfection (FIG. 6B).

The intracellular localization of mRNA is an important factor for successful gene therapy (Karp, J. M., and Peer, D. 2018. "Focus on RNA interference: from nanoformulations to in vivo delivery." In, 010201. IOP Publishing.). Moreover, the cationic lipid in the LNPs plays a key role in intracellular uptake and delivery. Typically, the hydrolytic enzymes and the acidic environment in the lysosome can degrade the carrier and the mRNA inside. Therefore, endosomal escape before mRNA degradation is considered a critical step for the success of mRNA therapy. Within the endosome, LNPs can undergo protonation, which leads to the fusion of their membrane lipids with the anionic lipids present in the endosome. Consequently, this enables the release of their mRNA cargo into the cytosol (Whitehead, K. A., et al. 2014. 'Degradable lipid nanoparticles with predictable in vivo siRNA delivery activity', Nature communications, 5: 4277.; Hou, X., et al. 2021. 'Lipid nanoparticles for mRNA delivery', Nature Reviews Materials, 6: 1078-94.). Herein, we studied the uptake and endosomal escape of OleSurf LNPs loaded with Cy5 mRNA in two different cell lines (FIGS. 7A-7F). The results showed the intracellular uptake of Cy5 mRNA loaded OleSurf LNPs as the red-fluorescent can be seen around the cell nucleus. Furthermore, after 4 hours of incubation, most of the green signal originating from the endosomes did not overlap with the red signal emitted by Cy5mRNA. This finding suggests that OleSurf LNPs effectively facilitated the release of mRNA into the cytosol. Hence, this observation is in agreement with reported studies where LNPs delivered mRNAs and released it inside the cells (Oberli, M. A., et al. 2017. 'Lipid nanoparticle assisted mRNA delivery for potent cancer immunotherapy', Nano letters, 17: 1326-35; Whitehead et al. 2014).

Figure 2A:
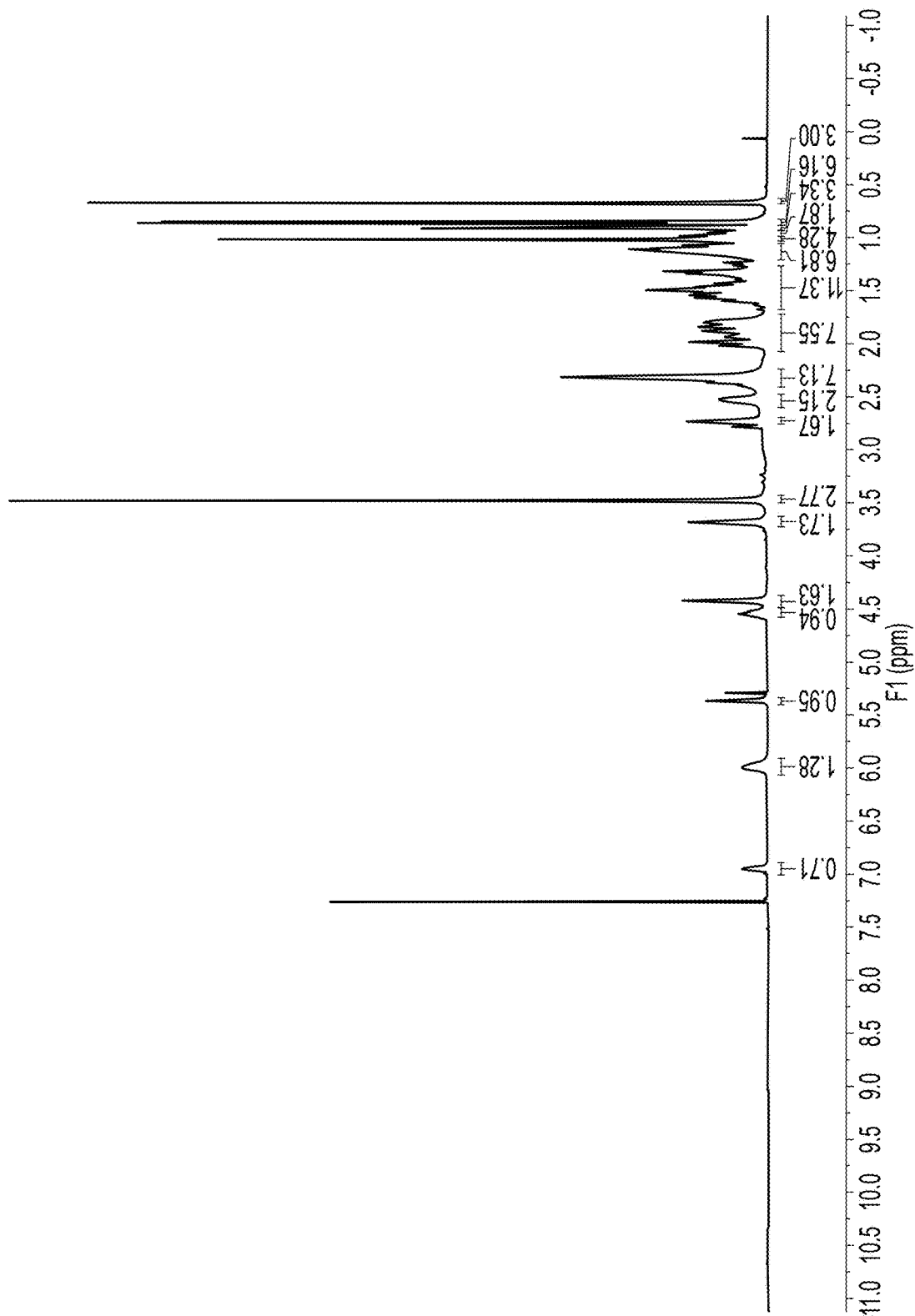
FIGS. 2A and 2B depict 1H nuclear magnetic resonance (NMR) spectrum of (2A) Surfactin, and (2B) Olesurf.
Figure 2B:
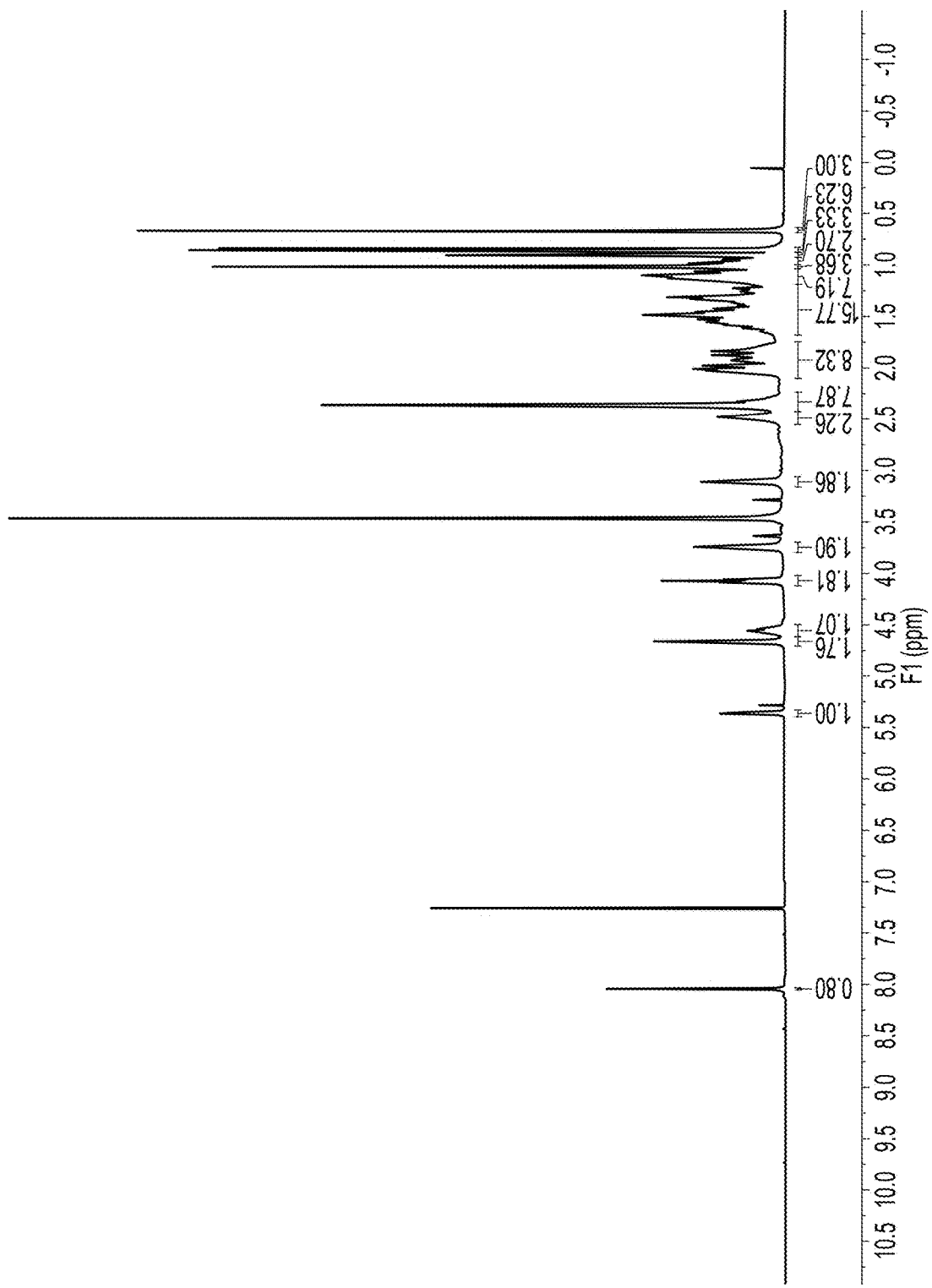
Figure 3A:
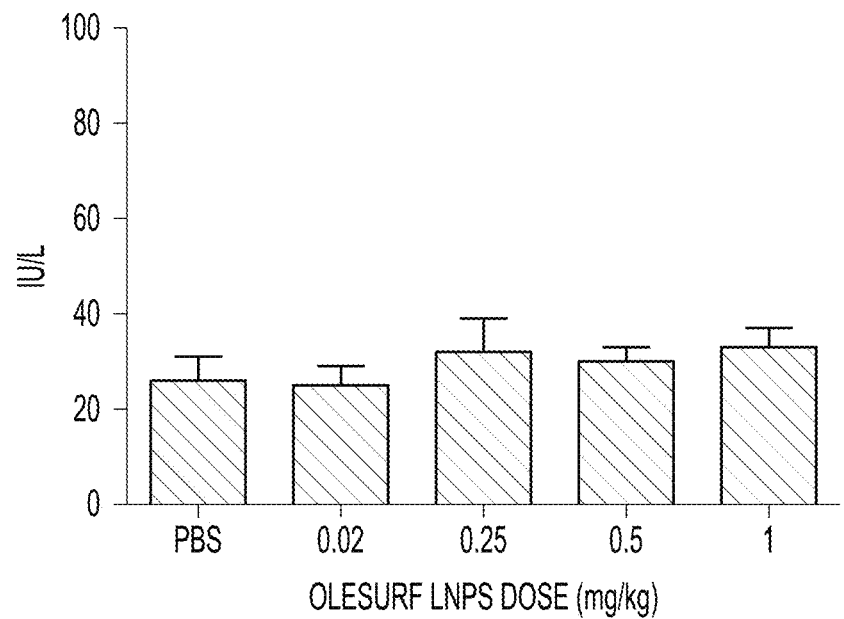
FIGS. 3A and 3B depict the evaluation of liver toxicology in mice 24 hours post injection of different LNPs doses, including (3A) serum profile analysis of alanine aminotransferase (ALT) levels and (3B) Serum profile analysis of aspartate aminotransferase (AST) levels.
Figure 3B:
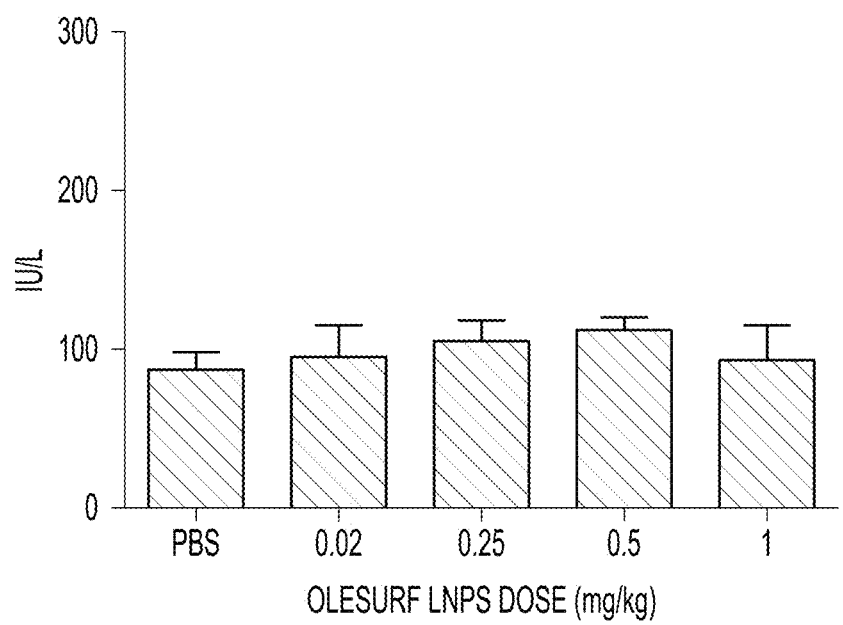

Safety is a crucial consideration before translating LNPs into the clinical stage (Ni et al. 2019; Hou et al. 2021). We evaluated whether the OleSurf-based LNPs demonstrated better biocompatibility in vivo. We assessed the liver toxicity and blood biocompatibility in relation to different doses of LNPs. For liver toxicity evaluation, we examined enzyme markers such as alanine transaminase (ALT) and aspartate aminotransferase (AST) in the bloodstream, along with histological analysis. LNPs were administered intravenously, and after 24 hours we measured ALT, and AST levels in the blood, while also subjecting liver samples to blinded histological examination. Following LNPs treatment, here is negligible elevation of liver enzyme at any dose level relative to the control and the enzyme levels remained within the normal range across all treatment groups (FIGS. 2A-2B). Additionally, the histological assessment of the liver samples did not reveal any signs of necrosis, significant bleeding, or other morphological alterations (FIGS. 3A-3B). These findings collectively indicate that the use of OleSurf LNPs does not induce liver toxicity. Nevertheless, it is crucial to conduct long-term toxicity assessments for LNPs, particularly when they are administered frequently for chronic diseases. Overall, our study confirms that these LNPs are both safe and effective for mRNA delivery.

In summary, we developed a novel LNP platform based on OleSurf for mRNA delivery. OleSurf can facilitate efficient encapsulation of mRNA and transfection in vitro. In addition, OleSurf LNPs protect mRNA molecules from degradation and facilitate their cellular uptake and release to the cytosol. Our in vivo results demonstrate the potential of OleSurf LNPs to deliver the mRNA in vivo. Moreover, the LNP were found to be a safe and non-toxic. The overall results of this study demonstrated the significant potential for OleSurf LNPs to be used as a highly efficacious delivery system for mRNA therapeutics.

It is to be understood that the surfactin-based lipopeptide for mRNA delivery is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A lipid nanoparticle platform for mRNA delivery prepared according to a method comprising:
   providing OleSurf lipids to form an organic phase;
   mixing a mRNA in 100 mM citrate buffer at pH 4 to form an aqueous phase; and
   mixing one part of the organic phase with three parts of the aqueous phase to obtain mRNA loaded lipid nanoparticles;
   purifying the mRNA loaded lipid nanoparticle platform using dialysis; and
   purifying the mRNA loaded lipid nanoparticle platform using centrifugal filtration.

2. The lipid nanoparticle platform for mRNA delivery of claim 1, wherein the lipid nanoparticle platform for mRNA delivery has an average particle size of 84.91±6.24 nm.

3. The lipid nanoparticle platform for mRNA delivery of claim 1, wherein the lipid nanoparticle platform for mRNA delivery has a polydispersity index of 0.102±0.025.

4. The lipid nanoparticle platform for mRNA delivery of claim 1, wherein the lipid nanoparticle platform for mRNA delivery has a zeta potential of +1.3±0.7.

5. The lipid nanoparticle platform for mRNA delivery of claim 1, wherein the lipid nanoparticle platform for mRNA delivery has an encapsulation efficiency of 90.51%±3.7%.

6. The lipid nanoparticle platform for mRNA delivery of claim 1, comprising making the OleSurf lipids by a method comprising:
   mixing surfactin dissolved in methanol with 2 mmol oleylamine to obtain a reaction mixture;
   adjusting the pH of the reaction mixture to 8.0 with NaOH;
   adding 10 ml dichloromethane to the reaction mixture under a nitrogen atmosphere;
   stirring the reaction mixture at about 25° C. for about 24 hours;
   concentrating the reaction mixture by evaporation; and
   purifying the reaction mixture using silica column chromatography to obtain the OleSurf lipids.

7. The lipid nanoparticle platform for mRNA delivery of claim 1, comprising purifying the mRNA loaded lipid nanoparticle platform using previously hydrated dialysis cassettes in 1× phosphate buffered saline solution for at least twelve hours.

8. The lipid nanoparticle platform for mRNA delivery of claim 1, comprising purifying the mRNA loaded lipid nanoparticle platform using centrifugal filtration using 10 kDa centrifuge filters at 3000 g for 60 minutes.

* * * * *